US00PP15503P2

(12) United States Plant Patent
Wilson

(10) Patent No.: US PP15,503 P2
(45) Date of Patent: Jan. 25, 2005

(54) ***VERBENA* PLANT NAMED 'MISS ANNE'**

(50) Latin Name: *Verbena canadensis*
Varietal Denomination: Miss Anne

(76) Inventor: Elizabeth Ann Wilson, 12430 Mary Ann Beach Rd., Fairhope, AL (US) 36532

( * ) Notice: Subject to any disclaimer, the term of this patent is extended or adjusted under 35 U.S.C. 154(b) by 31 days.

(21) Appl. No.: 10/783,270

(22) Filed: Feb. 19, 2004

(51) Int. Cl.[7] ..... A01H 5/00
(52) U.S. Cl. ..... Plt./308
(58) Field of Search ..... Plt./308

*Primary Examiner*—Anne Marie Grunberg
*Assistant Examiner*—Annette H Para

(57) ABSTRACT

A new variety of perennial *Verbena canadensis* named 'Miss Anne' characterized by vigorous spreading habit, dark green foliage, and large pure-white flowers. In combination these traits set 'Miss Anne' apart from all other existing varieties of *Verbena* known to the inventor.

2 Drawing Sheets

Genus: *Verbena*.
Species: *canadensis*.
Denomination: Miss Anne.

BACKGROUND OF THE INVENTION

The present invention relates to a new and distinct cultivar of *Verbena* (common name, Vervain) that is grown as an ornamental perennial and which is used in planters, hanging baskets or planted in the landscape. The new cultivar is known botanically as *Verbena canadensis* and will be referred to hereinafter by the cultivar name 'Miss Anne'.

Both prior to the inventor's discovery of 'Miss Anne' in 1992 and subsequently, the inventor, who is an experienced gardener and avid plant collector, had acquired or purchased from local and distant nursery and mail order sources, and had planted, a very large number of plants listed and described as perennial white *Verbenas*.

'Miss Anne' was discovered by the inventor in 1992 in a cultivated area of Lincoln County, Miss. The inventor was impressed by the unusually large flowers which were pure white in color, and the overall vigor of the plant compared to all other white *Verbenas* known to the inventor. The inventor is unable to determine the parental provenance of 'Miss Anne' but does consider after making careful observations and enquiries over ten years that 'Miss Anne' is a novel and exceptionally useful plant variety whose properties are listed within the Summary of the Invention herein.

The inventor considers that the closest comparison plant in respect of the combination of qualities of 'Miss Anne' is *Verbena canadensis* 'Homestead Purple' (unpatented) which is renowned for its perennial reliability in the south-eastern landscape. Apart from the difference in flower color, 'Miss Anne' is distinguishable from 'Homestead Purple' primarily as follows: 'Miss Anne' has more numerous and larger sized flowers, and a darker green and finer textured foliage which grows and spreads rapidly.

When compared with other white *Verbenas* in commerce, specifically the following varieties: *Verbena* 'Aztec White' (Balazwhit, U.S. Plant Pat. No. 13,943), *Verbena* 'Tortuga White' (Tort White, U.S. Plant Pat. No. 12,193), *Verbena* 'Tukana White' (Blancena, U.S. Plant Pat. No. 13,219) and *Verbena* 'Babylon White' (Vertis, U.S. Plant Pat. No. 12,288), 'Miss Anne' exhibits two main differences:

First, 'Miss Anne' tolerates frost and has survived in temperatures of 18 degrees Fahrenheit (USDA Zone 8) whereas the varieties listed above are variously described as intolerant of temperatures below freezing point.

Second, the inflorescence (umbel) of 'Miss Anne' is significantly larger in diameter than the infloresence of any of the varieties listed above. The infloresence diameter of 'Miss Anne' is typically 80 mm, whereas the infloresence diameters of the above varieties ranges between 30 mm and 60 mm.

The first asexual reproduction of 'Miss Anne' was conducted by the inventor in 1992 or 1993 in a cultivated area of Baldwin County, Ala. The method used for asexual propagation was softwood stem cuttings. The characteristics of the new cultivar have been observed by the inventor for more than ten years and are considered by the inventor to be stable and to have been reproduced true to type in successive generations.

SUMMARY OF THE INVENTION

The following traits have been repeatedly observed and represent the characteristics of the new *Verbena* cultivar 'Miss Anne'. These traits in combination distinguish 'Miss Anne' from all other commercial varieties known to the inventor. 'Miss Anne' has not been tested under all possible conditions and phenotypic differences may be observed with variations in environmental, climatic and cultural conditions.

1. *Verbena* 'Miss Anne' is a white-flowered perennial.
2. *Verbena* 'Miss Anne' exhibits large pure-white flower heads.
3. *Verbena* 'Miss Anne' exhibits fine textured dark green lemon-scented foliage.
4. *Verbena* 'Miss Anne' grows well in sun as well as partial shade in any well-drained soil.
5. *Verbena* 'Miss Anne' tolerates high heat and humidity, remaining free of disease expression.
6. *Verbena* 'Miss Anne' is easily propagated by softwood stem cuttings.
7. *Verbena* 'Miss Anne' is 30–35 cm. in mature height and may spread to 150 cm.

8. *Verbena* 'Miss Anne' is hardy in USDA Zone 8.
9. *Verbena* 'Miss Anne' blooms continuously year round in the South of the U.S., including consistent flowering during hot and humid summer months.

BRIEF DESCRIPTION OF THE DRAWINGS

The accompanying drawings illustrate the overall appearance of 'Miss Anne' growing under summer conditions out-of-doors in Pensacola, Fla. The displayed colors are as true as it is reasonably possible to obtain in colored reproductions of this type. Colors in the drawings may differ from the color values cited in the detailed botanical description, which more accurately described the actual colors of 'Miss Anne'.

The drawing labeled as FIG. 1 illustrates a six month old (from a struck cutting) plant in a 3 liter container in bloom from a top perspective.

Figure 1:
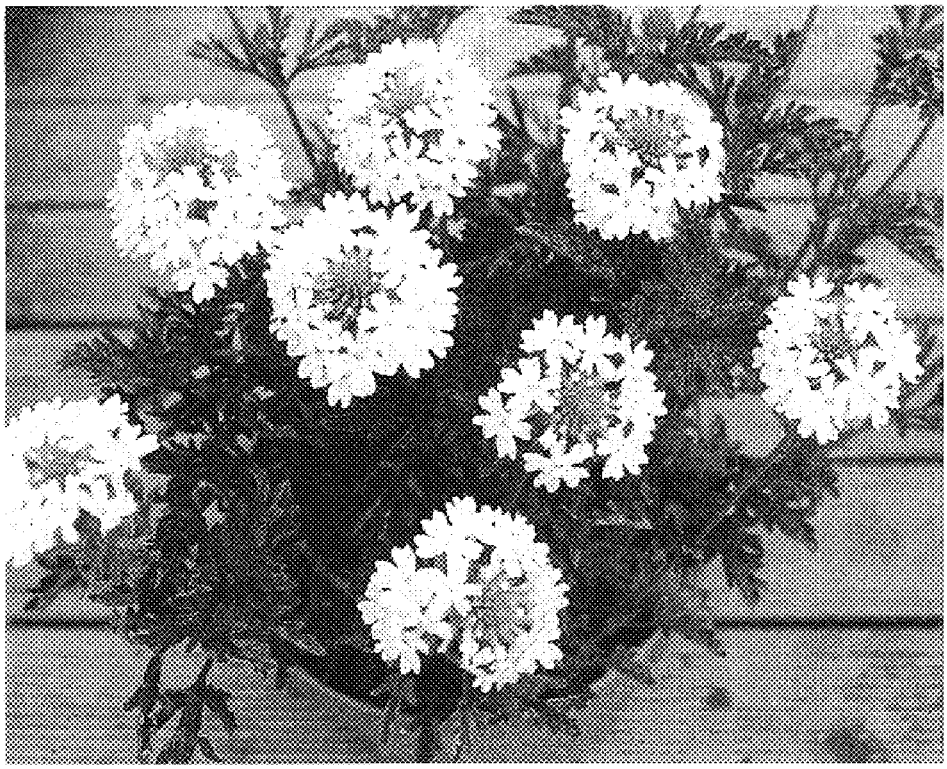
Figure 2:
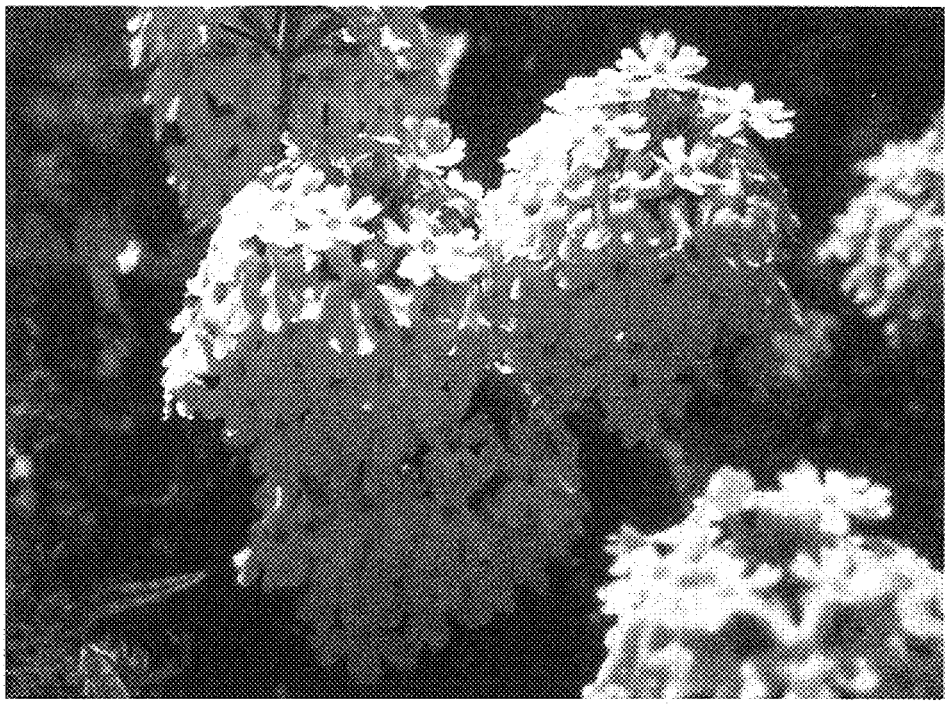

The drawing labeled as FIG. 2 illustrates a close-up view of the flower.

The drawings were made using conventional photographic techniques and although colors may appear different from actual colors due to light reflectance they are as accurate as possible by conventional photography.

BOTANICAL DESCRIPTION OF THE PLANT

The following is a detailed description of 'Miss Anne' when grown in a 1-liter container in Pensacola, Fla. The color determinations are in accordance with the 2001 edition of The Colour Chart of The Royal Horticultural Society, London, England, except where general color terms of ordinary dictionary significance are used.

Botanical classification: *Verbena canadensis.*
Species: *canadensis.*
Denomination: 'Miss Anne'.
Commercial classification: Herbaceous perennial.
Use: Ornamental for planter, hanging basket or landscape.
Container size: 1-liter container.
Plant dimensions (typical of growth in a 1 liter container): 46 cm. in width and 20 cm in height from the soil level.
Plant dimensions (mature plant in landscape): 100 cm–150 cm in width (spread) and 30 cm–35 cm in height from the soil level.
Cultural requirements: Plant in full sun or partial shade in any type of well-drained soil.
Special needs: None.
Resistance to pests and disease: Plant is highly resistance to insects and disease particularly thrips and mildew.
Parentage: Unknown.
Bloom period: Year round.
Plant habit: Spreading.
Vigor: Vigorous.
Sexuality: Bisexual.
Hardiness: Survives air temperature of 18 degrees F.: considered hardy in USDA Zone 8.
Root system: Fine, fibrous.
Propagation: Propagation is accomplished by softwood stem cuttings.
Time to develop roots: 7–10 days are needed for cuttings to develop roots, at an air and soil temperature of 75 degrees F.
Crop time: Approximately 4 weeks is needed to produce a finished 1-liter container.
Stem:
*Shape.*—Tetragonal.
*Stem color.*—137A.
*Stem dimensions.*—24 cm. in length and 2 mm. in diameter.
*Stem surface.*—Bristly.
*Branching.*—Basal branching and many spreading branches.
*Internode length.*—2.5–4.5 cm. between nodes.
Foliage:
*Type.*—Evergreen.
*Arrangement.*—Opposite.
*Shape.*—Sagittate.
*Margins.*—Deeply lobed and with serrated edges.
*Division.*—Pinnately compound.
*Venation.*—Pinnate with veins depressed on adaxial surface and protruding on abaxial surface.
*Texture.*—Medium to fine.
*Attachment.*—Petiolate.
*Leaf surfaces* (*adaxial and abaxial*).—Sparse short bristly hairs.
*Mature leaf dimensions.*—4.5 cm. in length and 3.0 cm. in width.
*Young leaf dimensions.*—2 cm. in length and 1 cm. in width.
*Leaf color* (*adaxial surface*).—137A.
*Leaf color* (*abaxial surface*).—138B.
*Petiole color.*—138B.
*Petiole surface.*—Bristly.
*Petiole dimensions.*—2.0 cm. in length and 1.5 mm. in width.
*Fragrance.*—Lemon scented.
Flowers:
*Inflorescence.*—Terminal inflorescence.
*Inflorescence shape.*—Drumstick shaped.
*Inflorescence dimensions.*—8 cm. in width at the widest part and 5.0 cm. in depth.
*Inflorescence type.*—Capitulum.
*Persistent or self-cleaning.*—Self-cleaning.
*Quantity of flowers per inflorescence.*—15–20 flowers per inflorescence.
*Lastingness of an individual inflorescence.*—2–3 weeks.
*Aspect.*—Facing upward and outward.
*Corolla depth.*—15 mm. in depth.
*Shape of corolla.*—Cylindrical.
*Color of corolla* (*inner surface*).—145D.
*Color of corolla* (*outer surface*).—145D.
*Nectary.*—Circular fringed area at opening of corolla.
*Fragrance.*—None.
*Bud dimensions.*—10 mm in length, and 2 mm in width.
*Bud shape.*—Ovate.
*Bud color, petals emerging.*—Pure white, lighter than 155A.
*Petals.*—Five in number.
*Petal color.*—(Adaxial and abaxial surfaces) pure white, lighter than 155A.
*Fused or unfused.*—Fused.
*Flower shape.*—Rotate.
*Flower dimension.*—1.50 cm. in diameter and 1.50 in height.
*Petal shape.*—Lobed.
*Petal margin.*—Entire.
*Petal surfaces.*—Glabrous and shimmering.
*Calyx.*—9 mm. in length and 3 mm. in width.
*Sepals.*—Five in number.
*Sepal dimensions.*—9 mm. in length and 1 mm. in width.

*Sepal apex.*—Apiculate.
*Fused or unfused.*—Sepals are fused midway.
*Sepal color.*—138B.
*Sepal surface.*—Stipitate glandular with long hairs.

Reproductive organs:
*Stamens.*—Four stamens inserted inside corolla tube.
*Stamen color.*—155A.
*Pollen color.*—145C.
*Stamen dimensions.*—2 mm. in length and 0.50 mm. in width.
*Pollen amount.*—Small amount.
*Anther dimensions.*—Less than 0.50 mm. in height and 1 mm. in width.
*Anther shape.*—Double wings.
*Anther color.*—145C.
*Ovary position.*—Superior.
*Ovary dimensions.*—Less than 0.25 mm. in diameter and height.

Seed production:
*Seed shape.*—The seed is round and held at the end of a filament.
*Seed color.*—197A.
*Seed dimensions.*—Less then 0.25 mm. in diameter.
*Dimensions of filament.*—1.75 mm. in length and less than 0.25 mm. in width.
*Filament color.*—156D.
*Number of seeds.*—More than one hundred.

It is claimed:

1. A new and distinct cultivar of *Verbena* plant named 'Miss Anne' as described and illustrated herein.

* * * * *